US009161831B2

(12) United States Patent
Farag (10) Patent No.: US 9,161,831 B2
(45) Date of Patent: Oct. 20, 2015

(54) LOCKING MECHANISM FOR SECURING THE INTERFACE BETWEEN STENT GRAFTS

(71) Applicant: Cook Medical Technologies LLC, Bloomington, IN (US)

(72) Inventor: Jacqueline Farag, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 52 days.

(21) Appl. No.: 14/180,637

(22) Filed: Feb. 14, 2014

(65) Prior Publication Data

US 2015/0230915 A1    Aug. 20, 2015

(51) Int. Cl.
| | | |
|---|---|---|
| *A61F 2/07* | (2013.01) | |
| *A61F 2/852* | (2013.01) | |
| *A61F 2/848* | (2013.01) | |
| *B29C 65/00* | (2006.01) | |
| *A61F 2/82* | (2013.01) | |
| *A61F 2/915* | (2013.01) | |

(52) U.S. Cl.
CPC . *A61F 2/07* (2013.01); *A61F 2/848* (2013.01); *A61F 2/852* (2013.01); *B29C 66/50* (2013.01); *A61F 2002/075* (2013.01); *A61F 2002/826* (2013.01); *A61F 2002/828* (2013.01); *A61F 2002/8486* (2013.01); *A61F 2002/91591* (2013.01)

(58) Field of Classification Search
CPC ............... A61F 2/07; A61F 2002/075; A61F 2002/826; A61F 2002/828; A61F 2002/823; A61F 2/852; A61F 2002/91591

USPC ........................................................ 623/1.35
See application file for complete search history.

(56) References Cited

U.S. PATENT DOCUMENTS

| | | | |
|---|---|---|---|
| 5,741,293 | A | 4/1998 | Wijay |
| 7,160,318 | B2 | 1/2007 | Greenberg et al. |
| 2004/0225349 | A1 | 11/2004 | Thistle et al. |
| 2006/0178733 | A1 | 8/2006 | Pinchuk et al. |
| 2009/0270971 | A1 | 10/2009 | Xiao et al. |

FOREIGN PATENT DOCUMENTS

| | | |
|---|---|---|
| WO | WO 98/53761 | 12/1998 |
| WO | WO 2004/016193 A2 | 2/2004 |

OTHER PUBLICATIONS

European Search Report for corresponding EP 15275031.1 dated Jul. 17, 2015, 6 pages.

*Primary Examiner* — David Isabella
*Assistant Examiner* — Suba Ganesan
(74) *Attorney, Agent, or Firm* — Brinks Gilson & Lione (57) ABSTRACT

A modular stent graft system and methods of assembly are disclosed. The stent graft assembly comprises a first stent graft having an interface region at its distal end and a first locking stent secured to an internal surface of the interface region. A second stent graft having an interface region at its proximal end is configured to at least partially overlap with the interface region at the distal end of the first stent graft. The second stent graft comprises a second locking stent secured to an external surface of the interface region. The first and second locking stents are configured to be engaged such that the second locking stent is nested between the first locking stent and an internal surface of the interface region of the first stent graft thereby interlocking the first and second stent grafts to each other.

13 Claims, 5 Drawing Sheets

LOCKING MECHANISM FOR SECURING THE INTERFACE BETWEEN STENT GRAFTS

TECHNICAL FIELD

The present invention relates to medical devices and more particularly to endovascular stent grafts.

BACKGROUND OF THE INVENTION

The functional vessels of human and animal bodies, such as blood vessels and ducts, occasionally weaken or even rupture. For example, in the aortic artery, the vascular wall can weaken or tear, resulting in dangerous conditions such as aneurysm and dissection. Treatment of such conditions can be performed by implanting a prosthesis within the vascular system using minimally invasive surgical procedures. An endoluminal prosthesis typically includes one or more stents affixed to graft material and is delivered to the treatment site by endovascular insertion utilizing introducers and catheters. Once the endoluminal prosthesis is radially enlarged, it should remain in place indefinitely by self-attachment to the vessel wall, acting as a substitute vessel for the flow of blood or other fluids.

Treatment of vascular conditions near a branch point with an endoluminal prosthesis is sometimes required. Typically, an endoluminal prosthesis for use near a bifurcation will have a main lumen body, for placement within the main aorta for example, and two branch lumens extending from the main lumen body into the branch arteries such as the iliac branch arteries. One such bifurcated prostheses is a single piece prosthesis. Such unitary structures have a main tubular body and pre-formed leg extensions. However, a more common alternative to the single piece approach is the use of a modular system. In these systems, one or both of the leg extensions can be provided separately and attached to a bifurcated distal end of the main tubular body to provide the final prosthesis. Examples of modular systems are described in PCT Patent Application Publication WO98/53761 and in U.S. Pat. No. 7,160,318, which are incorporated herein by reference. Known methods for attaching the main tubular body and the leg extensions includes, in one example, reliance on radial force and friction between the respective graft materials, which creates force for preventing the two parts from moving and/or pulling apart once they have been positioned and radially expanded in a desired location within the vasculature. In addition to such friction fit, the disclosed locking mechanism facilitates a secure seal and attachment between the bifurcated distal end of the main body stent graft and the proximal end of the leg extension(s), thus allowing the respective components to be locked together in a desired position within the vasculature.

SUMMARY

The present disclosure describes a modular stent graft system and methods of assembly. In one example, a modular stent graft system is disclosed. The stent graft system comprises a first stent graft comprising a first tubular body of biocompatible graft material, a proximal end, a distal end and a first interface region having an internal surface and an external surface at the distal end. The first stent graft further comprises a first self-expanding locking stent secured to the internal surface of the first interface region, the first locking stent comprising a series of proximal apices and a series of distal apices, a proximal end having a first diameter and a distal end having a second diameter greater than the first diameter, wherein the first locking stent is secured to the internal surface of the first interface region only at the distal stent apices. The system further comprises a second stent graft comprising a second tubular body of biocompatible graft material, a proximal end, a distal end and a second interface region having an internal surface and an external surface at the proximal end configured to at least partially overlap with the first interface region. A second self-expanding locking stent is secured to the external surface of the second interface region, the second locking stent comprising a series of proximal apices, a series of distal apices, a proximal end having a first diameter and a distal end having a second diameter greater than the first diameter, wherein the second locking stent is secured to the external surface of the second interface region only at the proximal stent apices. The first locking stent is configured to receive the second locking stent in an interlocking relationship.

A method of assembling a modular stent graft system is also disclosed. In one example, the method comprises providing a first stent graft comprising a first tubular body of biocompatible graft material, a proximal end, a distal end and a first interface region having an internal surface and an external surface at the distal end; a first self-expanding locking stent secured to the internal surface of the first interface region, the first locking stent comprising a series of proximal apices and a series of distal apices, a proximal end having a first diameter and a distal end having a second diameter greater than the first diameter, wherein the first locking stent is secured to the internal surface of the first interface region only at the distal stent apices. The method further comprises providing a second stent graft comprising a second tubular body of biocompatible graft material, a proximal end, a distal end and a second interface region having an internal surface and an external surface at the proximal end configured to at least partially overlap with the first interface region; a second self-expanding locking stent secured to the external surface of the second interface region, the second locking stent comprising a series of proximal apices, a series of distal apices, a proximal end having a first diameter and a distal end having a second diameter greater than the first diameter, wherein the second locking stent is secured to the external surface of the second interface region only at the proximal stent apices. At least a portion of the proximal end of the second stent graft is inserted into the distal end of the first stent graft so that the first and second interface regions at least partially overlap. The method further comprises allowing the second stent graft to expand and engaging the first and second locking stents such that the distal apices of the second locking stent are nested between the first locking stent and the internal surface of the interface region of the first stent graft.

DETAILED DESCRIPTION

Throughout this specification, the terms proximal and proximally are used to refer to a position or direction towards the patient and/or to be inserted into a patient's body orifices or cavities and the terms distal and distally are used to refer to a position or direction away from, or even external to a patient's body. While the description below is directed to endovascular prostheses used within the abdominal aorta and iliac arteries for treatment of aortic aneurysm, use in any other body lumens and/or vessels, for example, the thoracic aorta and/or branch or peripheral vessels, the gastrointestinal tract, ducts and orifices is also contemplated.

Figure 2:
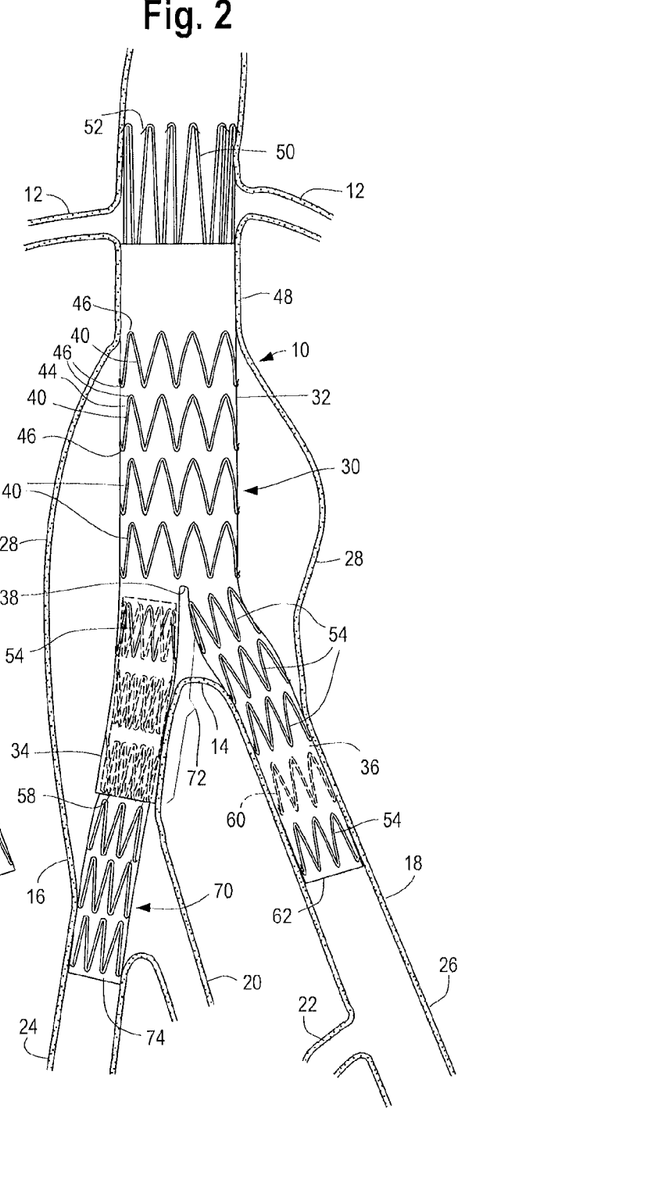
FIG. 2 illustrates the modular stent graft of FIG. 1 positioned in a patient's vasculature, with the bifurcated main body portion in the abdominal aorta and the leg extension extending into an iliac artery.

Now looking more closely at the drawings and more particularly FIG. 2, a schematic view of the vasculature of a patient is illustrated, particularly showing the aorta and aortic bifurcation extending down towards the iliac arteries. The vasculature comprises an aorta 10 in the region between the renal arteries 12 and the aortic bifurcation 14. Common iliac arteries 16 and 18 extend from the aortic bifurcation 14. The common iliac arteries 16 and 18 each bifurcate into internal iliac arteries 20 and 22 and external iliac arteries 24 and 26 respectively. The aorta 10 is shown as having an aneurysm 28 which extends towards the aortic bifurcation 14.

To traverse the aneurysm 28, a bifurcated aortic stent graft 30 has been deployed into the aorta 10. The bifurcated aortic stent graft 30 comprises a main tubular body 32 of a biocompatible graft material. Examples of biocompatible graft materials include polyesters, such as poly(ethylene terephthalate), and fluorinated polymers, such as polytetrafluoroethylene (PTFE) and expanded PTFE. Examples of biocompatible polyesters include DACRON (DUPONT, Wilmington, Del.) and TWILLWEAVE MICREL (VASCUTEK, Renfrewshire, Scotland). Other examples of biocompatible materials include extracellular matrix (ECM) materials, such as a purified collagen-based matrix derived from submucosa tissue.

The graft material may be made of a single material, or it may be a blend, weave, laminate or composite of two or more materials. The graft material may also include other additives, such as plasticizers, compatibilizers, surface modifiers, biological materials such as peptides and enzymes, and therapeutic agents such as drugs or other medicaments. The particular graft material on any one portion of the graft may be the same, or the materials may be different. The bifurcated stent graft 30 has a short leg 34 and a long leg 36 extending from a bifurcation 38. One example of a bifurcated stent graft includes the Zenith LP stent graft available from COOK, INC. (Bloomington, Ind.).

Figure 1:
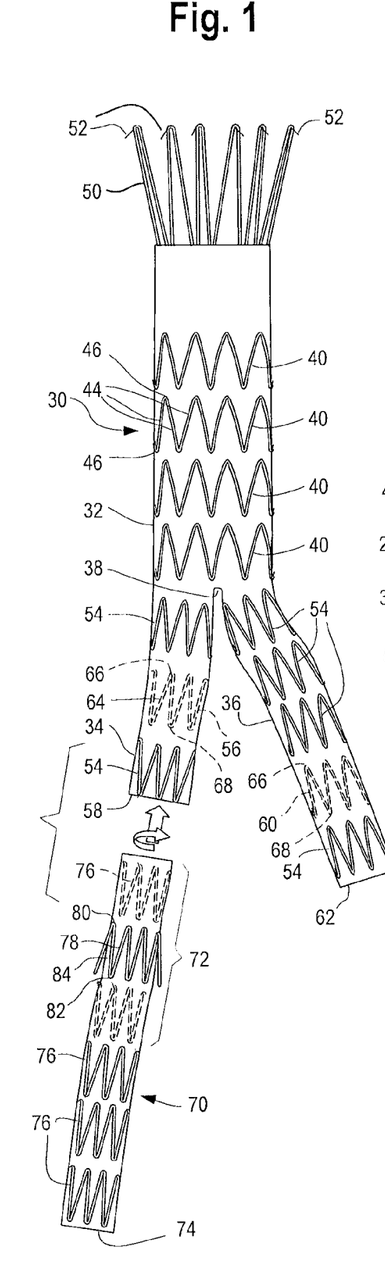
FIG. 1 is illustrates one example of a modular endovascular stent graft comprising a bifurcated main body portion and a leg extension.

The graft material 32 is secured to and supported by one or more stents 40. For example, standard surgical suturing techniques 42 can be used to secure the graft material 32 to a stent 40. A stent 40 can be positioned on the interior of the tubular graft material, or it can be positioned on the exterior of the graft material as shown in FIGS. 1 and 2. In another example, a stent can be sandwiched between two layers of graft material, and this stent may also be secured by sutures 42.

The stents 40 may have a wide variety of configurations and may be balloon-expandable or self-expanding. Typically, stents have a circular or cylindrical cross-section when fully expanded, so as to conform to the generally circular cross-section of a body lumen. For example, the stents may be discrete stents having a zig-zag configuration in which straight struts 44 are set at angles to each other and are connected by acute bends or apices 46. The struts are thus connected into an endless loop, forming a generally tubular structure as shown in FIGS. 1 and 2. Discrete zig-zag stents are also referred to as Gianturco stents or Z-stents such as the Z-STENT available from COOK, INC. (Bloomington, Ind.). In another example, the stents may contain individual stent segments that are connected to provide an elongated, flexible stent. The individual stent segments can have a variety of configurations, including the zig-zag configuration. A specific example of a connected zig-zag stent is the ZILVER™ stent also available from COOK, INC.

Stents 40 may be made of any rigid biocompatible material, such as metal, plastic or ceramic. Preferably the stents are made of a metal, such as stainless steel, nitinol, and other biocompatible alloys. Stents may be equipped with one or more barbs to secure the prosthesis to the vessel wall or to another component of the prosthesis. If the stent 40 is secured to the graft material 32 by suturing, the sutures 42 may be positioned along struts 44 and/or at the bends or apices 46 of the stent 40. For stents having a zig-zag configuration, it may be desirable to employ a suture at least one of the apices 46, or alternatively, a suture 42 at each apex 46 of the stent 40 to further increase the stability of the connection. The stents 40 illustrated in FIGS. 1 and 2 are preferably manufactured from a shape memory alloy, including, for example, nitinol, such that it can be loaded on to a delivery device in a radially compressed configuration which then self-expands upon deployment within the vasculature of a patient as shown in FIG. 2.

Turning back now to FIG. 2, the proximal end 48 of the bifurcated stent graft 30 is engaged with a non-aneurysed portion of the aorta 10 just distal of the renal arteries 12. To ensure good fixation the stent graft 30 includes, in one non-limiting example, a supra renal exposed stent 50 with barbs 52 engaging the wall of the aorta 10 proximal of the renal arteries 12. It is also contemplated, however, that other known methods of fixation may be utilized to secure the stent 30 in a desired location within the vasculature, and more particularly, to secure the proximal end 48 of the aortic stent graft 30 within the aorta 10.

As FIGS. 1 and 2 illustrate, stents 40 have been shown as external stents which are sutured to the external surface of the main body of the graft 32. Furthermore, one or more stents are secured the graft material along the lengths of both the short leg 34 and long leg 36. More specifically, short leg 34 and long leg 36 have one or more longitudinally spaced stents 54. As shown, short leg 34 has one external stent 54 distal of the bifurcation 38 followed by one internal stent 56 and then another external stent 54 at the distal most end 58 of the short leg 34. Long leg 36 is shown as having three external stents 54 distal of the bifurcation 38 followed by one internal stent 60 and another external stent 54 at the distal most end 62 of the long leg 36. The stents 54 secured to the short and long legs 34, 36 are generally cylindrical, with the exception of the internal stents 56, 60 located near the distal ends 58, 62 of the legs 34, 36.

Figure 3:
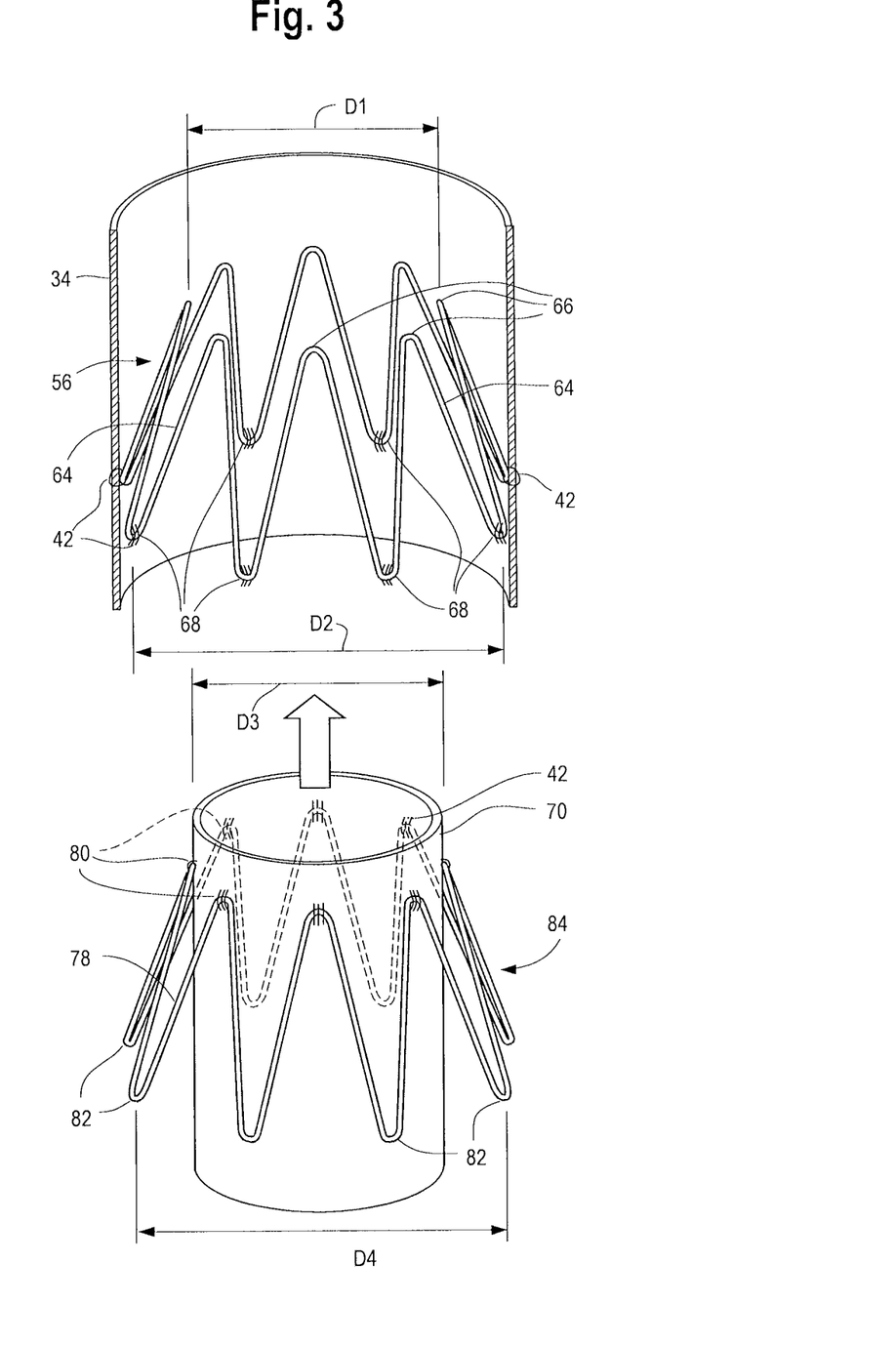
FIG. 3 is an enlarged view of one example of a locking stent at the distal end of the main body portion configured to engage with a locking stent at the proximal end of a leg extension.

More specifically, the internal stents 56, 60 secured near the distal end 58, 62 of short leg 34 and long leg 36 may, in one example, may be flared or formed into a frusto-conical configuration thus forming an internal connection or "locking stent" which may provide for enhanced sealing and attachment between the respective first and second legs 34, 36 and any additional leg extension prosthesis as described in further detail below. The internal locking stent 56 on short leg 34 is preferably substantially similar in shape and configuration to internal locking stent 60 on long leg 36, thus the description of internal locking stent 56 similarly applies to internal locking stent 60 unless otherwise noted. Internal stent 56 preferably comprises struts 64 and proximal apices 66 and distal apices 68 between the struts 64. In one example, the internal locking stent 56 may be made by conventional manufacturing process such that it is initially a cylindrical shape and then formed into a frusto-conical cone shape such as by heat treatment. Internal stent 56 may be secured to the graft material of legs 34 and/or 36 by a suture 42 or similar attachment means at one or more of the distal stent apices 68 such that it flares radially inwardly from the suture/graft attachment point 42 in a proximal direction. In other words, the internal locking stent 56 may be "cone shaped" with one or more of the distal-most apices 68 being sutured to the graft and forming the widest diameter D2 and the proximal-most stent apices 66 being flared radially inwardly therefrom (thus having the narrowest diameter D1 at the proximal apices 66). While FIG. 3 shows all of the proximal stent apices 66 being flared radially inwardly to form a frusto-conical configuration, it is also contemplated that only selected apices 66 are flared inwardly. For example, only one stent apex 66, or a pair of apices 66 (whether adjacent apices, alternating apices or opposing apices) may be inwardly flared, while the remaining "non-flared" apices retain a substantially cylindrical shape.

As shown in FIG. 2 the short leg 34 of the bifurcated aortic stent graft 30, may not extend distally down to or much beyond the aortic bifurcation 14. Therefore, an iliac leg extension piece 70 may be provided for connection to the short leg 34. The external proximal sealing surface 72 of the iliac leg extension piece 70 is configured to provide an interface to seal within the lumen of the short leg 34 of the bifurcated stent graft 30 while the distal end 74 of the iliac leg extension piece 70 may engage in a sealing manner into a non-aneurysed, healthy portion of the common iliac artery 16 and/or external iliac artery 24.

Alternatively, in the case where an aneurysm extends down into the external iliac artery 24, the iliac leg extension piece 70 may serve as a bridge which extends between the short leg 34 of the bifurcated aortic stent graft 30 and the proximal end of another stent graft component, i.e., a branched iliac stent graft (not shown). Such a branched iliac stent graft would extend distally beyond any such aneurysm so that its distal end may engage in a sealing manner with a non-aneurysed portion of the external iliac artery 24.

FIG. 2 illustrates the long leg 36 of the bifurcated stent graft 30 extending distally into the common iliac artery 18, such that the distal end 62 of long leg 36 is engaged with a healthy, non-aneurysed portion of common iliac artery 18. However, if necessary or desired (such as in the event that an aneurysm extends down into the common iliac artery 18 distally of the long leg 36 and/or into the external iliac artery 26), then another iliac extension piece (not shown) like that of iliac leg extension piece 70 may be provided that sealingly connects to the long leg 36 of the stent graft 30 for extending distally into the common iliac artery 18, or even further into the external iliac artery 26. Thus, description of iliac leg extension piece 70 that sealingly connects to short leg 34 may similarly apply to any additional leg extension piece that is attached to long leg 36.

One example of iliac leg extension piece 70 is illustrated in further detail in FIG. 1. As shown there, iliac leg extension piece 70 is preferably a tubular body of biocompatible graft material. One or more stents 76 are secured to the graft material along the length of leg extension 70. It is noted that leg extension piece 70 (or any additional leg extension piece that is attached to long leg 36) can be of a variety of dimensions (i.e., varying lengths and/or widths) depending upon the requirements of a particular situation, the geometry of a patient's vasculature and the location of deployment. Hence, the number of stents 76 along the length of the tubular body of leg extension 70 can vary. There may be one, two or more self-expanding stents 76 that are located on the inside and/or on the outside of the tubular graft material. In one example, the stents are preferably self-expanding Z-stents having a zig-zag configuration in which straight struts 78 are set at angles to each other and are connected by acute bends or apices 80, 82.

As shown in FIGS. 1 and 2, the stents 76 secured to the graft material of leg extension 70 are generally cylindrical in nature, with the exception of external stent 84. External stent 84 secured near the proximal end 72 of leg extension 70 may, in one example, be flared such that it is frusto-conical or cone-shaped, thus forming a connection or locking stent. Locking stent 84 is configured to lock with or otherwise connect to the correspondingly configured frusto-conical locking stent 56 within the lumen of short leg 34 as described in further detail below.

More particularly, the frusto-conical external locking stent 84 may be secured to the graft material of leg extension 70 by a suture 42 or similar attachment means, at one or more of the proximal stent apices 80, and flare radially outwardly therefrom in a distal direction. In other words, the stent may be "cone shaped" with one or more of the most proximal apices 80 being sutured to the graft (and having the narrowest diameter D3) and the distal-most stent apices 82 being flared radially outwardly (and having the widest diameter D4). While FIG. 3 shows all of the distal locking stent apices 82 being flared radially outwardly, it is also contemplated that only selected apices 82 are flared outwardly. For example, only one stent apex 82, or a pair of apices 82 (whether adjacent apices, alternating apices or opposing apices) may be outwardly flared, while the remaining "non-flared" apices retain a substantially cylindrical shape.

The proximal end 72 of the leg extension 70 extends at least partially into the lumen of the short leg 34 such that an overlap or interface exists between the distal end 58 of short leg 34 and the proximal end 72 of leg extension 70. The leg extension 70 may then be locked into place when the internal flared locking stent 56 near the distal end 58 of short leg 34 engages the external flared locking stent 84 near the proximal end 72 of leg extension 70, as described in further detail below.

In one non-limiting example of use, the main bifurcated stent graft 30 can be delivered and deployed within a patient's aorta 10 and leg extension 70 sealingly connected to short leg 34 (and any additional leg extension sealingly connected to long leg 36 if necessary and desired) as follows. First, a main graft such as the bifurcated aortic stent graft 30 can first be delivered to a treatment site using a variety of endovascular techniques. In treating aortic aneurysms, a catheter-based introducer, such as those available from COOK, INC. (Bloomington, Ind.) can be used to insert a compressed endovascular prosthesis (such as stent graft 30) into the body through a femoral artery and then into the aorta 10.

Figure 15:
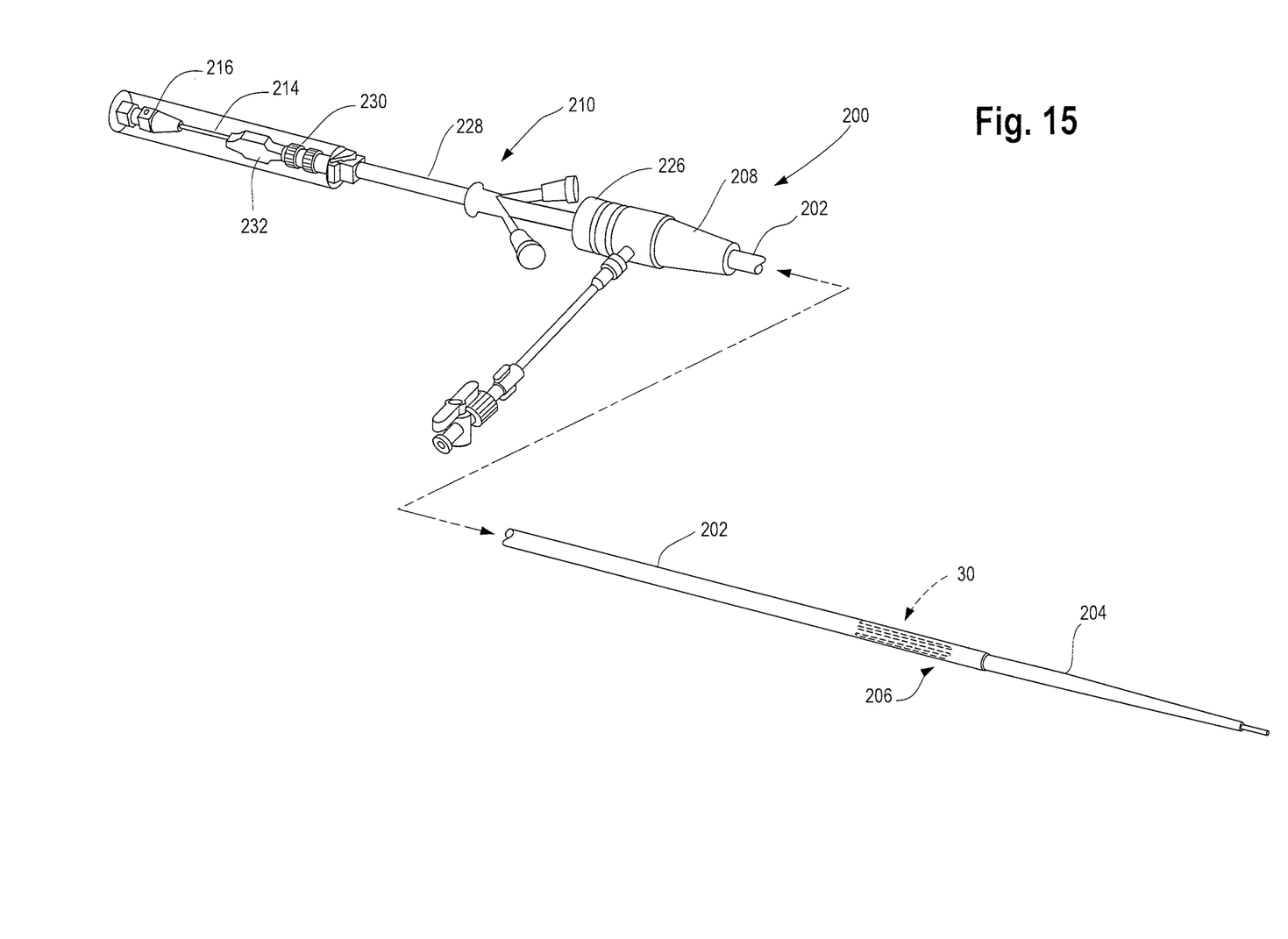
FIG. 15 illustrates one example of an introducer for delivery and deployment of one or more of the modular stent graft components.

Referring to FIG. 15, one example of an introducer 200 for the bifurcated aortic stent graft 30 may include a delivery sheath 202 surrounding stent graft 30 which is carried by tapered dilator 204 at proximal end 206, and a fitting 208 at distal end 210 of the delivery system. Inner cannula 214, which is connected to handle 216, extends from the tapered dilator 204 to distal end 210. The introducer 200 may also include check-flow valve 226, pusher 228, pusher fitting 230 and pin vise 232. Once the introducer has been inserted into the patient's vasculature and the aortic stent graft 30 positioned in its desired location, the delivery sheath 202 can then be pulled back towards the distal end 210 of the delivery system 200 and any diameter-reducing ties removed so that the stent graft 30 is deployed within the aorta 10. Commonly, the longer leg 36 is deployed in the ipsilateral iliac artery and the shorter leg 34 deployed in the contralateral iliac artery, with the bifurcation 38 of stent graft 30 seated adjacent to the aortic bifurcation 14.

Figure 4:
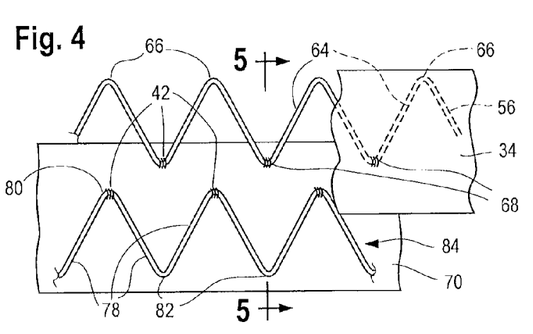
FIG. 4 illustrates one example of assembly of a modular stent graft whereby the proximal end of the leg extension is inserted into the distal end of the main body portion and before the respective locking stents are engaged.
Figure 5:
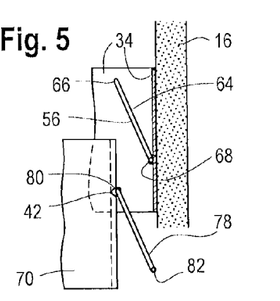
FIG. 5 is a side cross-sectional view of FIG. 4.
Figure 6:
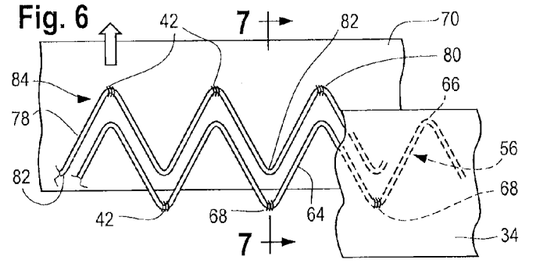
FIG. 6 illustrates the proximal end of the leg extension being moved in a proximal direction during insertion of the leg extension into the distal end of the main body portion and before the locking stents are engaged.
Figure 7:
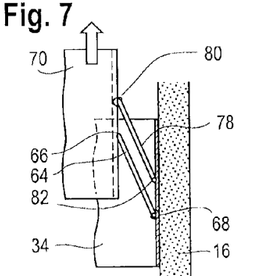
FIG. 7 is a side cross-sectional view of FIG. 6.
Figures 12, 13, 14:
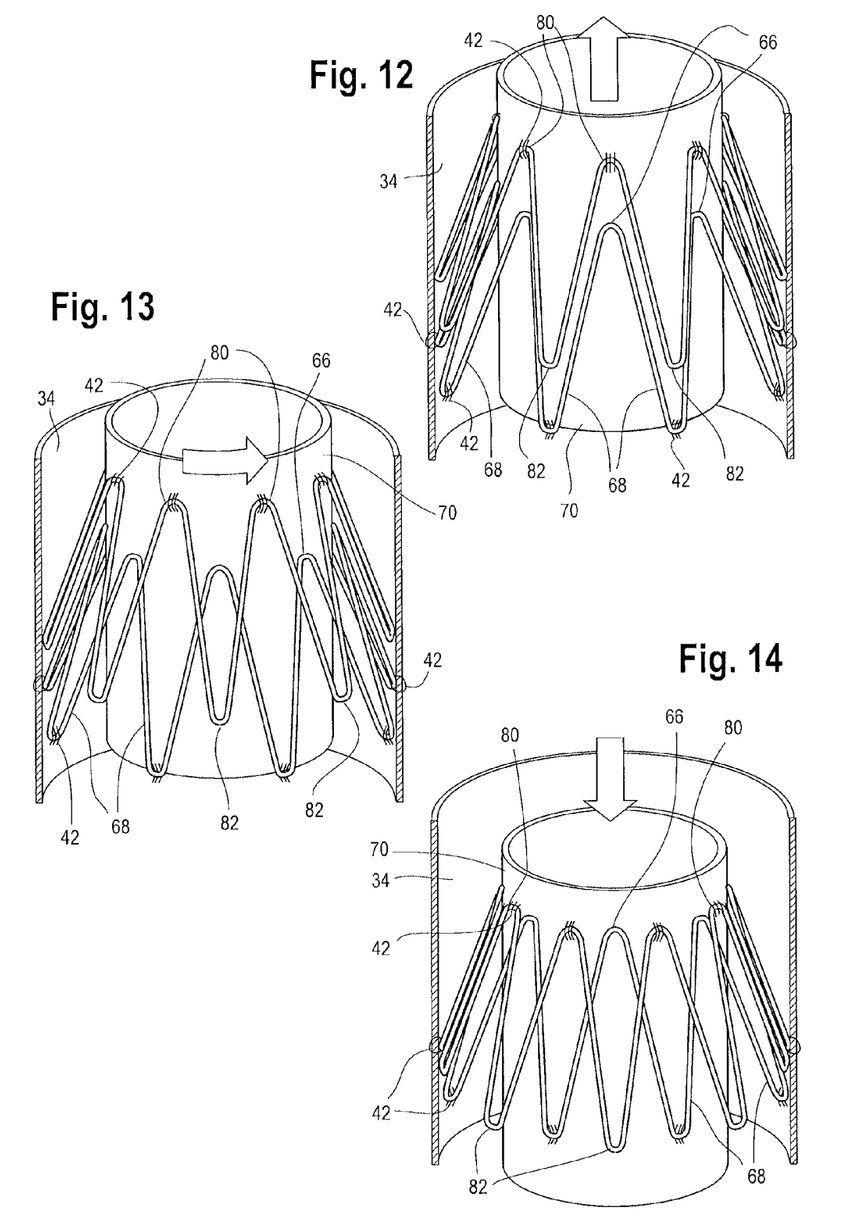
FIG. 12 is an enlarged view of the proximal end of a leg extension being inserted in a proximal direction into the distal end of the main body stent graft and before the respective locking stents are engaged.
FIG. 13 illustrates the leg extension being rotated relative to the main body stent graft to align the respective locking stents for interlocking engagement.
FIG. 14 illustrates the leg extension being pulled distally after the respective locking stents have been properly aligned for interlocking engagement.

With the bifurcated aortic stent graft 30 deployed and in place in the aorta 10, an iliac leg extension piece 70 may then be delivered to a treatment site, such as iliac artery 16 illustrated in FIG. 2, using a variety of known endovascular techniques. For example, another catheter based introducer 200 may be used to insert a compressed prosthesis such as leg extension 70 into the vasculature so that the proximal end 72 of leg extension 70 is located within the lumen of short leg 34. Preferably, the internal flared locking stent 56 near the distal end 58 of short leg 34 is aligned with the external flared locking stent 84 near the proximal end 72 of leg extension 70. Radiopaque markers or other indicators may be used to facilitate proper placement and alignment of leg extension 70 with short leg 34. In one example, the proximal end 72 of leg extension 70 can initially be moved in a proximal direction within the lumen of short leg 34 so that the external flared locking stent 84 of leg extension 70 moves beyond (i.e., proximally past) the internal flared locking stent 56 of short leg 34 as shown in FIGS. 4, 6 and 12. The sheath 202 covering the leg extension 70 on the delivery device may then be withdrawn so that leg extension at least partially radially outwardly expands within the lumen of short leg 34.

Figure 10:
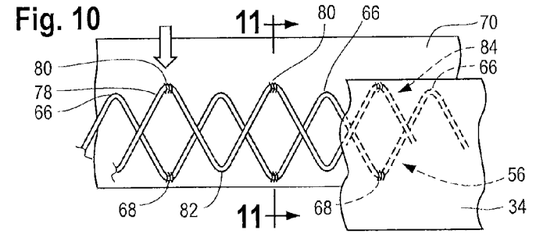
FIG. 10 illustrates the locking stent at the proximal end of the leg extension engaged with the locking stent at the distal end of the main body portion, thus interlocking the leg extension stent graft with the bifurcated main body stent graft.

The physician may then pull back slightly on the leg extension 70 in a distal direction as shown in FIG. 10 and FIG. 14 until the internal flared locking stent 56 near the distal end 58 of short leg 34 engages and/or otherwise locks with the external flared locking stent 84 near the proximal end 72 of leg extension 70. Locking may be determined in various ways, such as, for example, the physician sensing resistance when pulling distally on the leg extension 70. In other words, when locking occurs, the outwardly flared distal apices 82 of the locking stent 84 on leg extension 70 become nested and securely braced between the graft material of short leg 34 and the inwardly flared proximal apices 66 of the locking stent 56 of short leg 34 as shown in FIGS. 10, 11 and 14.

Figure 8:
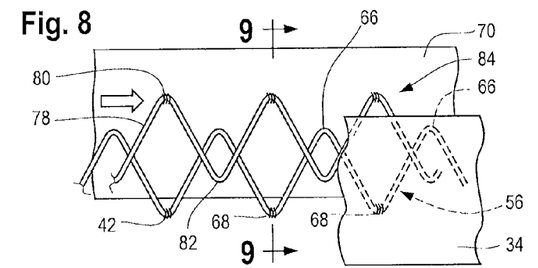
FIG. 8 illustrates rotation of the leg extension stent graft relative to the distal end of the main body portion to align the respective locking stents for interlocking engagement.
Figure 9:
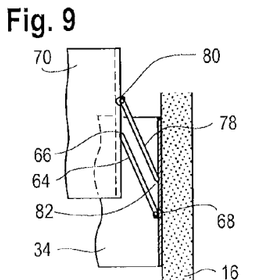
FIG. 9 is a side cross-sectional view of FIG. 8.
Figure 11:
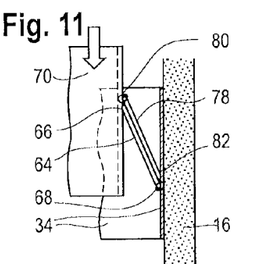
FIG. 11 is a side cross-sectional view of FIG. 10.

If the respective two locking stents 56, 84 are not initially properly aligned so that locking does not occur, the leg extension 70 may be at least partially pulled back into the sheath 202 and the introducer rotated in one or more small increments as shown in FIGS. 8 and 13 and the leg extension 70 redeployed until proper alignment of the respective locking stents 56, 84 and locking therebetween is achieved as shown in FIGS. 10, 11 and 14. In order for the locking stents to become "unlocked," the leg extension 70 must be pushed proximally at least until the distal apices 82 of the locking stent 84 on leg extension 70 have moved proximally away from and beyond the proximal apices 66 of locking stent 56 in short leg 34, thus allowing the two locking stents 56, 84 to be disengaged.

If necessary or desired, the delivery and deployment of an additional iliac leg extension, such as a leg extension for connection to long leg 36, may be accomplished in a manner similar to that described above. For example, an additional leg extension may be delivered to a treatment site (such as iliac artery 18) by a delivery catheter 200 and the proximal end of the additional leg extension positioned within the lumen of long leg 36. An external locking stent 84 on the proximal end of such an additional leg extension may then engage and lock with an internal locking stent 60 within long leg 36, thus providing a secure connection between the respective stent grafts.

With the main bifurcated graft 30 and one or more iliac leg extensions 70 connected to one or both of short leg 34 and/or long leg 36, delivery of the complete modular endovascular prosthesis is accomplished. As is evident in FIG. 2, there is overlap where the graft material at the proximal end 72 of iliac leg extension 70 interfaces with the short leg 34 when the leg extension 70 has been deployed. The stents at the proximal end 72 of iliac leg extension 70 self expand, thereby pressing against the inner surface of the lumen of the short leg 34 of the bifurcated prosthesis 30. This overlap of graft material establishes a friction fit connection between the two stent graft components 30, 70. In addition to this friction fit, the attachment and sealing engagement of one or more iliac leg extensions (such as leg extension 70) to the legs 34, 36 of the bifurcated prosthesis 30 at the implantation site is further enhanced by the locking engagement between the respective locking stents 56, 84. As a non-limiting example, the described locking mechanism provided by the locking stents may reduce the risk of leg extension separation by increasing the pull out force needed to separate the respective components 30, 70, thus reducing or substantially eliminating endoleaks that may result from pull apart between a main body stent graft 30 and the leg extensions 70.

While the description above describes the locking stent 84 on leg extension 70 to be an external stent and the locking stent 56 within short leg 34 to be an internal stent, it is also contemplated that any of the stent placements may be reversed and relocated. In one non-limiting example, one or more internal stents within the lumen of leg extension 70 may be arranged to engage and lock with one or more external stents on either short leg 34 or long leg 36.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. A modular stent graft system comprising
a first stent graft comprising a first tubular body of biocompatible graft material, a proximal end, a distal end and a first interface region having an internal surface and an external surface at the distal end;
a first self-expanding locking stent secured to the internal surface of the first interface region, the first locking stent comprising a series of proximal apices and a series of distal apices, a proximal end having a first diameter and a distal end having a second diameter greater than the first diameter, wherein the first locking stent is secured to the internal surface of the first interface region only at the distal stent apices;
a second stent graft comprising a second tubular body of biocompatible graft material, a proximal end, a distal end and a second interface region having an internal surface and an external surface at the proximal end configured to at least partially overlap with the first interface region;
a second self-expanding locking stent secured to the external surface of the second interface region, the second locking stent comprising a series of proximal apices, a series of distal apices, a proximal end having a first diameter and a distal end having a second diameter greater than the first diameter, wherein the second locking stent is secured to the external surface of the second interface region only at the proximal stent apices;
wherein the first locking stent is configured to receive the second locking stent in an interlocking relationship.

2. The stent graft system of claim 1 wherein at least a portion of the second locking stent is nested between the first locking stent and the internal surface of the interface region of the first stent graft when the first and second locking stents are interlocked.

3. The stent graft system of claim 1 wherein the proximal end of the second stent graft is sealingly engaged with the distal end of the first stent graft when the first and second locking stents are interlocked.

4. The stent graft system of claim 1 wherein the proximal apices of the first locking stent are proximal to and circumferentially aligned with the distal apices of the second locking stent when the first and second locking stents are interlocked.

5. The stent graft system of claim 1 wherein the second stent graft comprises a leg extension stent graft configured for placement in the iliac artery.

6. The stent graft system of claim 1 wherein the first stent graft comprises a bifurcated stent graft configured for placement in the abdominal aorta.

7. The stent graft system of claim 1 wherein the distal end of the first stent graft is bifurcated and comprises a first leg and a second leg.

8. The stent graft system of claim 7 wherein the first locking stent is secured to at least one of the first and second leg.

9. The stent graft system of claim 8 wherein a third locking stent is secured to the other of the first and second leg.

10. The stent graft system of claim 9 further comprising a third stent graft comprising a third tubular body of biocompatible graft material, a proximal end, a distal end and a third interface region having an internal surface and an external surface at the proximal end;
a fourth self-expanding locking stent secured to the external surface of the third interface region, the fourth locking stent comprising a series of proximal apices, a series of distal apices, a proximal end having a first diameter and a distal end having a second diameter greater than the first diameter, wherein the fourth locking stent is secured to the external surface of the third interface region only at the proximal stent apices; and
wherein the third locking stent is configured to receive the fourth locking stent in an interlocking relationship.

11. A method of assembling a modular stent graft system comprising;
providing a first stent graft comprising a first tubular body of biocompatible graft material, a proximal end, a distal end and a first interface region having an internal surface and an external surface at the distal end; a first self-expanding locking stent secured to the internal surface of the first interface region, the first locking stent comprising a series of proximal apices and a series of distal apices, a proximal end having a first diameter and a distal end having a second diameter greater than the first diameter, wherein the first locking stent is secured to the internal surface of the first interface region only at the distal stent apices;
providing a second stent graft comprising a second tubular body of biocompatible graft material, a proximal end, a distal end and a second interface region having an internal surface and an external surface at the proximal end configured to at least partially overlap with the first interface region; a second self-expanding locking stent secured to the external surface of the second interface region, the second locking stent comprising a series of proximal apices, a series of distal apices, a proximal end having a first diameter and a distal end having a second diameter greater than the first diameter, wherein the second locking stent is secured to the external surface of the second interface region only at the proximal stent apices;
inserting at least a portion of the proximal end of the second stent graft into the distal end of the first stent graft so that the first and second interface regions at least partially overlap;
allowing the second stent graft to expand;
interlocking the first and second locking stents such that the distal apices of the second locking stent are nested between the first locking stent and the internal surface of the interface region of the first stent graft.

12. The method of claim 11 further comprising rotating the first and second stent grafts with respect to each other until the proximal apices of the first locking stent are circumferentially aligned with the distal apices of the second locking stent prior to the step of interlocking.

13. The method of claim 11 wherein the first and second stent grafts are interlocked when the first and second locking stents are engaged.

* * * * *